United States Patent [19]

Mignot

[11] Patent Number: 5,569,853
[45] Date of Patent: Oct. 29, 1996

[54] ULTRASONIC MEASURING APPARATUS WHICH MINIMIZES THE NUMBER OF DIGITAL VALUES TREATED BY PROCESSING MEANS

[75] Inventor: Jean-Pierre Mignot, Peseux, Switzerland

[73] Assignee: Asulab S.A., Bienne, Switzerland

[21] Appl. No.: 146,404

[22] Filed: Nov. 1, 1993

[30] Foreign Application Priority Data

Nov. 2, 1992 [FR] France ................................... 92 13351

[51] Int. Cl.$^6$ ................................................ G01N 29/04
[52] U.S. Cl. ............................................. 73/602; 364/508
[58] Field of Search ........................... 73/602, 622, 627, 73/615, 625; 128/661.01, 661.09, 660.01, 661.03, 661.04, 661.05, 661.06, 661.1; 364/413.25, 507, 508

[56] References Cited

U.S. PATENT DOCUMENTS

| | | | |
|---|---|---|---|
| 3,699,318 | 10/1972 | Underkoffler et al. | 364/719 |
| 4,173,007 | 10/1979 | McKeighen | 73/625 |
| 4,324,141 | 4/1982 | Stearn | 73/627 |
| 4,509,526 | 4/1985 | Barnes | 128/661.1 |
| 5,179,383 | 1/1993 | Raney | 342/25 |
| 5,383,366 | 1/1995 | Wallingford | 73/602 |

FOREIGN PATENT DOCUMENTS

| | | |
|---|---|---|
| 0324855 | 1/1989 | European Pat. Off. . |
| 0356629 | 3/1990 | European Pat. Off. . |

OTHER PUBLICATIONS

Noninvasive measurement of arterial diameters in humans using ultrasound echoes with prefiltered waveforms, Medical And Biological Engineering And Computing, vol. 25, No. 2, Mar. 1987, Stevenage GB, pp. 189–194.

*Primary Examiner*—Christine K. Oda

[57] ABSTRACT

An ultrasonic measuring apparatus that includes an ultrasonic transducer for emitting ultrasonic pulses at a predetermined repetition frequency towards an object having a plurality of walls such as a blood vessel, receiving echoes reflected from such walls, and producing an echo signal having a plurality of elementary echo components ($E_{ant}$, $E_{post}$). A digitizer digitizes the echo signal into a series of digital values that are stored in a buffer memory under control of a circuit. A computer transfers the series of digital values stored in the buffer memory into a memory. The computer is programmed to process the digital values stored in the memory in the period between consecutive pulses and to remove a group of the digital values digitized between consecutive elementary components ($E_{ant}$, $E_{post}$) from those digital values to be treated between such consecutive pulses.

10 Claims, 3 Drawing Sheets

PRIOR ART

ULTRASONIC MEASURING APPARATUS WHICH MINIMIZES THE NUMBER OF DIGITAL VALUES TREATED BY PROCESSING MEANS

BACKGROUND OF THE INVENTION

The present invention relates generally to ultrasonic measuring apparatus which emit an ultrasonic pulse towards an object having walls, receive echos reflected from said walls, and subsequently treat signals created in response to these echos, so as so determine the temporal positions of said walls.

The invention is suitable for use in medical applications, and may be used, for example, to follow the temporal movement of the position the anterior and posterior walls of a blood vessel and determine the changes in the inner diameter and in the thickness of the walls of the blood vessel with time. Whilst it will be convenient to disclose the invention in relation to that exemplary application, it is to be appreciated that the invention is not limited to that application. The invention may, for example, be used in the measurement of the thickness of the corneal lens or in the non-invasive measurement of other bodily organs.

FIG. 1 represents schematically a known manner of measuring the position of the walls of a blood vessel. This figure shows an ultrasonic transducer 1 placed above the skin 2 of a subject, which transducer 1 faces an artery 3 displayed in cross-section. The transducer 1 is controlled by an electronic circuit so as to emit an ultrasonic pulse 4, to receive ultrasonic echos resulting from the reflection of that pulse on the artery-tissue and artery-blood interfaces, and to create an echo signal in response thereto. Depending on the frequency of the ultrasonic transducer, this echo signal can represent four distinct echos 5, 6, 7 and 8, or only two echos corresponding respectively to a combination of the echos 5 and 6, and to a combination of the echos 7 and 8.

The movement of each interface is determined in the following manner. The transducer 1 emits a pulse 4 with a repetition frequency of generally between 10 Hz and 5 kHz. In order to follow the position of the echos, which are detected by the transducer after a delay which depends on the position of each interface, a temporal window of fixed size is used to define a time interval in which the echos are awaited, and which is adjusted, after each cycle, so that the echos would be detected in the center of that window if the interfaces were immobile.

Knowledge of the temporal position of each interface as well as the propogation speed of the pulse in the blood and the tissue makes it possible, by measuring the interval, to determine the change of the inner diameter and the thickness of the anterior and posterior walls of the blood vessel 3 with time.

FIG. 1 is a schematic diagram only. In practice, the echos resulting from reflection of an impulse on the anterior and posterior walls of the blood vessel 3 are not as pure, but have a much more complex form as is shown by the elemental echos $E_{ant}$ and $E_{post}$ in FIG. 2. This deformation results from the fact that the ultrasonic pulse traverses tissues having different characteristics and from the fact that the interface between the wall of a blood vessel and the surrounding tissue is not as clearly defined as, for example, the interface between a metal plate and the surrounding air.

The position of the interfaces causing these echos, notably in the medical domain, thus cannot be directly and automatically determined from the form of the echo signal.

Several techniques are known for detecting the position of the moving interfaces.

According to a first technique, the position of the interfaces is manually determined. The user displays the echo signal on an oscilloscope or another display means and choses a particular point on the echo signal onto which the echo tracker must lock. Unfortunately, this technique requires that great experience on the part of the user to determine the particular point of the elemental echo which corresponds to the position of the interface. In practice, the user choses either the peak having the greatest amplitude or the central peak of the elemental echo. There is no assurance that the point chosen effectively corresponds to the position of the interface.

A second technique consists of processing the echo signal so as to suppress the noise, only keeping the part of the signal resulting from the reflection of the ultrasonic signal on each interface. This technique, however, presents the inconvenience that the digital signal processing is not able to be realised in real time. In fact with the calculating means now available the treatment of the signals received during the opening of the temporal window takes in the order of 0.1 to 5 seconds whereas, with a pulse repetition frequency of 500 Hz, the time available for treating the echo signal, and performing associated operations such as reading and controlling peripheral devices, is in the order of 0.002 seconds.

It is necessary then to procede in two stages: in a first period, to digitize and store in real time the echo signals to be studied and, in a second period, to treat these echo signals. It can be seen that this technique presents three inconveniences, which are the necessity to have a large amount of memory, the time taken to treat the echo signals and the absence of control in real time of the data as it is acquired.

Swiss patent application no. 2871/91, which corresponds to U.S. Pat. No. 5,297,552, describes an ultrasonic measuring apparatus which addresses the problems of this second technique. That apparatus emits a first ultrasonic pulse towards a blood vessel, converts the echo signal created from the echos detected by the transducer into a series of digital values (created during the opening of the temporal window) which are then stored. In an initialisation stage, these stored digital values are treated so as to select a reference point in each elemental echo of the echo signal, determine for each elemental echo the temporal position of each interface producing that elemental echo, and calculate for each elemental echo the temporal interval between the position of the reference point of that elemental echo and the temporal position of the interface obtained by the processing.

In parallel with this treatment, an assimilation phase occurs in which the digital values resulting from the detection of echo signals from subsequent ultrasonic pulses are treated so as to track the temporal position of the reference points from each echo signal.

There follows then an acquisition phase in which the temporal position of each interface corresponding to each elemental echo of echo signals resulting from ultrasonic pulses subsequent to the assimilation phase are followed and memorized. Finally, an exploitation stage occurs during which the data memorized in the acquisition phase is used to provide information to the user, such as displaying the diameter of the blood vessel as a function of time.

It will be appreciated by those skilled in the art that various other techniques may be used in conjunction with the present invention to determine the position of the interfaces in the echo signals.

Whilst the technique described in Swiss patent application no. 2871/91 avoids the need to process each digitized echo signal so as to determine the position of each interface in each elemental echo of the echo signal in real time, some treatment of each digitized echo signal between consecutive ultrasonic pulses is nevertheless required.

In this technique each echo signal, digitized during the opening of the temporal window, needs to be treated so as to track the selected reference points on the elemental echos. In order to enable this tracking to occur, each reference point must fall within that part of the echo signal digitized during the opening of the temporal window.

Display of each echo signal received may be provided both prior to and during the intitialisation, assimilation and processing stages so that the user can verify the correct positioning of the transducer on the skin of the subject and monitor the form of the echo signals. Processing means control this display in real time. Each digital value corresponding to each echo signal needs to be read from a memory location, and adjusted for characteristics such as magnification, delay and offset. The processing means must also create a curve of "best-fit" for these digital values.

A peripheral device such as a keyboard may also be used to provide user control over the display of each echo signal and any associated graphical information which is also displayed The processing means must provide the keyboard control to enable input signals to be read from such a device. Further measuring equipment, such as a sphygmanometer, a plethysmograph or a Doppler sensor may be connected to the processing means. The signals from this equipment may be required to be sampled, read and displayed concurrently with each echo signal received from the ultrasonic transducer. In addition, the processing means must control all functions associated with the memory in which the digital values are stored.

Time is also required between consecutive pulses to perform the necessary calculations in each of the initialisation, assimilation and processing stages.

The time required to perform the above-described processing is related to the speed of the processing means and the number of values digitized from each echo signal during the opening of the temporal window. The rate at which an echo signal is sampled so as to enable its accurate reconstruction is determined by the fundamental frequency of the echo signal. In the case of echo signals resulting from the reflection of ultrasonic impulsions from blood vessels, such a sampling frequency may be 100 MHz, that is, the echo signal is sampled every 10 nanoseconds.

A humeral artery can have a diameter as small as 4 mm. The echos from the walls of a humeral artery will thus occur relatively quickly after each other. It has been found that an echo signal resulting therefrom needs only in the order of 500 digital values at a sampling frequency of 100 MHz to enable accurate reconstruction. However, a femoral or carotid artery may have a diameter in excess of 1 cm. The echos from its walls will thus be further apart, and more than 1500 digital values may be needed to accurately recover the corresponding echo signal.

The processing means used to treat these digitized values may be provided by a microprocessor, the most powerful of which available today operates at 32 MHz. The time required for an instruction cycle (often about 10 machine cycles) in such microprocessors is about 0.4 μsec, and several instruction cycles are needed to treat each digital value in the manner described above. If the ultrasonic pulse produced by the transducer is repeated at a frequency of 500 Hz, less than 6000 instruction cycles may be performed between consecutive pulses.

It can be seen that for large arteries, existing microprocessors are not able to treat a sufficient number of digital values from an echo signal in the time between consecutive pulses so as to include the elemental echos produced by both walls of the artery. The tracking of the reference points on the echo signals, the display of the echo signals, the required user control and processing of the echo signal thus cannot be properly performed. Whilst a more powerful main-frame computer could be used in these applications, the much greater cost of such computers is prohibitive.

SUMMARY OF THE INVENTION

It is an object of the present invention to provide an ultrasonic measuring apparatus which alleviates or overcomes the disadvantages of the prior art.

With that object in mind, the present invention provides an ultrasonic measuring apparatus comprising an ultrasonic transducer for emitting an ultrasonic pulse at a predetermined repetition frequency towards an object having a plurality of walls, receiving echos reflected from said walls, and producing an echo signal having a plurality of elementary echo components, digitizing means for digitizing said echo signal into a series of digital values, a buffer memory for storing said digital values from said digitizing means, control means for transferring said digital values from said digitizing means into said buffer memory, memory means for storing said digital values from said buffer memory, and processing means for transferring said series of digital values stored in said buffer memory into said memory means, said processing means being adapted to treat said digital values stored in said memory means between consecutive pulses, characterised in that said processing means is further adapted to remove a group of said digital values digitized between consecutive elementary echo components from those digital values to be treated between consecutive pulses.

The number of digital values from each echo signal which need to be processed in real-time between consecutive ultrasonic pulses is thus minimized, and the range of blood vessel diameters which may be measured by existing apparatus correspondingly increased.

The following description refers in more detail to the various features of the ultrasonic measuring apparatus of the present invention. In order to facilitate an understanding of the present invention, reference is made in the description to the accompanying drawings where the ultrasonic measuring apparatus is illustrated in a preferred embodiment. It is to be understood that the ultrasonic measuring apparatus of the present invention is not limited to the preferred embodiment as illustrated in the drawings.

DESCRIPTION OF PREFERRED EMBODIMENTS

Figure 1:
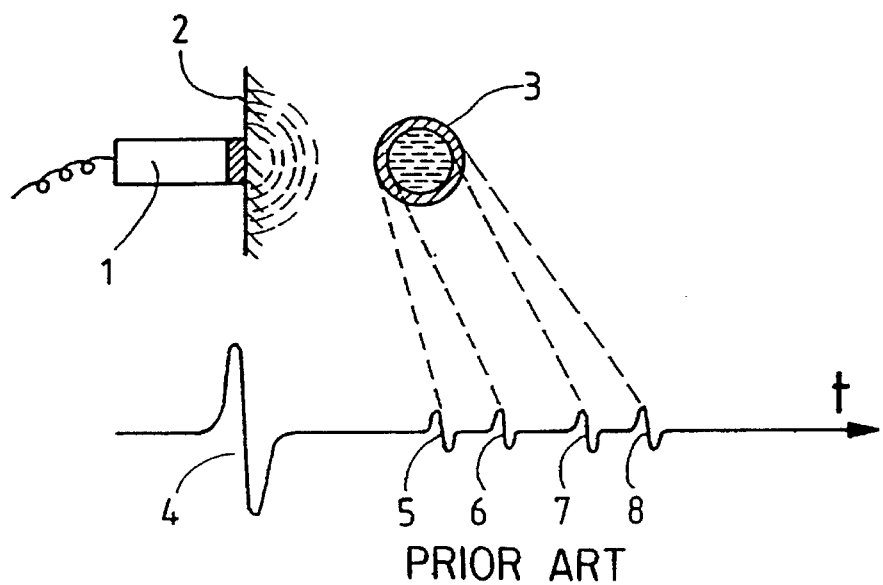
FIG. 1, already described, illustrates the principle of ultrasonic measurement of the position of the interfaces of the anterior and posterior walls of a blood vessel.
Figure 2:
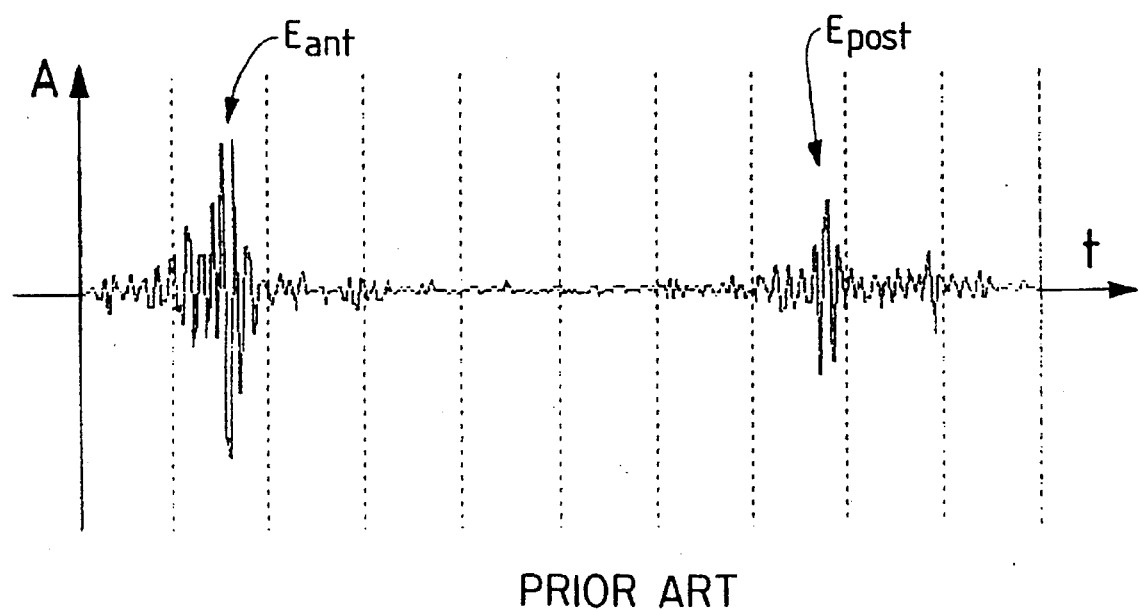
FIG. 2, already described, illustrates the temporal shape of an echo signal representing two elemental echos produced by the anterior and posterior walls of a blood vessel.
Figure 3:
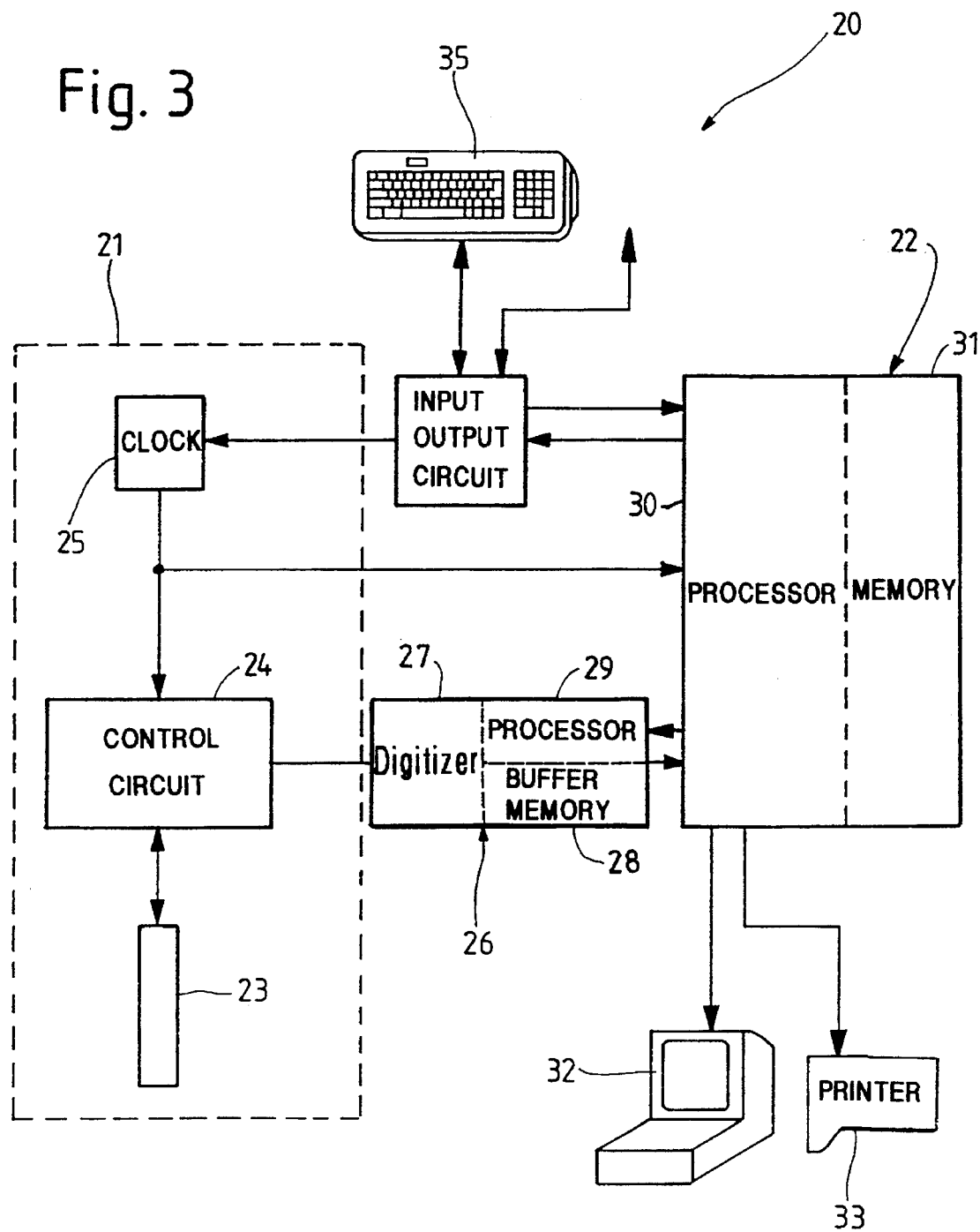
FIG. 3 shows diagramatically one embodiment of an ultrasonic measuring apparatus according to the present invention.

Referring now to FIG. 3 of the drawings, there is shown an ultrasonic measuring apparatus 20 comprising an ultrasonic transducer 21 and a calculating device 22. The ultrasonic transducer 21 has an ultrasonic probe 23 for transmitting an ultrasonic signal and receiving the echos resulting from the reflection of this ultrasonic wave, a control circuit 24 for controlling the ultrasonic probe 23 and a clock 25. The latter delivers to the control circuit 24 a signal defining the frequency of repetition of the interrogation signal emitted by the ultrasonic probe 23.

The control circuit 24 comprises a transmitter circuit delivering an electrical impulse which is transformed by the ultrasonic probe 23 into a corresponding ultrasonic signal, and a receiving circuit receiving the electrical signal delivered by the ultrasonic probe 23 corresponding to the ultrasonic echo signal received by the ultrasonic probe 23. The control circuit 24 and the ultrasonic probe 23 are of a conventional type. The central frequency of the ultrasonic impulse is chosen as a function of the intended application. It may be, for example, from 2 to 20 MHz.

The electrical echo signal delivered by the control circuit 24 is received by the processing device through an analog-digital converter 26. It is possible to use for this purpose a product of the type STR 8100 from SONIX Inc. (Springfield, Va., USA) which is an analog-digital 8 bit converter capable of processing up to $10^8$ calculations/second. The analog-digital converter comprises a digitizer 27, a buffer memory 28 and a processor 29. The digitizer 27 converts the analog echo signal received from the control circuit into a series of digital values for storage in the buffer memory 28. The processor 29 controls the operation of the digitizer 27, the storage of the digital values in the buffer memory 28 and the transfer of the stored digital values to the calculating device 22.

The calculating device 22 has an echo tracker which is used in a conventional manner to track the temporal position of each elemental echo of an echo signal in relation to the ultrasonic signal transmitted. This position, that is ultimately the delay in each elemental echo signal from the ultrasonic pulse transmitted, varies with the distance between the ultrasonic probe and the mobile interfaces from which the ultrasonic impulse is reflected. To carry out this tracking, the echo tracker of the calculating device 22 receives the clock signal produced by the clock 25 and delivers to the analog-digital converter 26 a delay signal to start digitization of the echo signal at a suitable moment. The echo tracker is preferably of the peak detection type (positive or negative) of the digitized echo signal. This peak is not the correct value for assessing movment of the mobile walls since the distance between two sampling points is equal to $c/(2.f)$ where c=1540 m/s (the speed of ultrasonic waves in the medium) and f=100 MHz is the sampling frequency. It is possible to follow the displacement of the echo only roughly.

Alternatively, the echo tracker could be of the crossover detection type such as described in EP-A-337 297 and EP-A-356 629.

The calculating device 22 implements the measuring process to determine the the temporal position of the interfaces of the blood vessel 3. To do this it has, as main components, processing means 30 and memory means 31. The processing means 30 is advantageously a personal computer with an 80X387 or 80X486 type processor. Various peripheral apparatus may be added, such as display means 32, printing means 33 and an input/output circuit 34, the latter allowing the user to control the operation of the measuring apparatus 20 via a keyboard 35 or other user input device. The input-output circuit 34 may also be connected to the clock 25 to control the frequency of repetition of the clock signal from the calculating device 22. It may also serve to synchronize other measuring equipment such as a sphygmomanometer, a plethysmograph or a Doppler sensor in order to measure the blood pressure and blood rate.

The operation of the ultrasonic measuring apparatus 20 to determine the temporal inner diameter and wall thickness of the blood vessel 3 will now be described.

Before beginning measurements per se, the user selects the parameters of the apparatus, such as the repetition frequency and the sensor type, i.e. the central frequency of the ultrasonic pulse. These parameters may be selected via the keyboard 35, or automatically by the processing means 30 as a function of the application chosen by the user. By way of example, in the event of measuring the internal diameter and the thickness of the blood vessel wall, the repetition frequency is in the order of 10 Hz to 5 kHz for the measurement of the carotid artery. The duration of the delay transmitted to the analog-digital converter 26 is also adjusted, either manually or automatically, so that the elemental echos of the echo signals may be placed within the temporal window and each echo is correctly tracked by the echo tracker.

Figure 4:
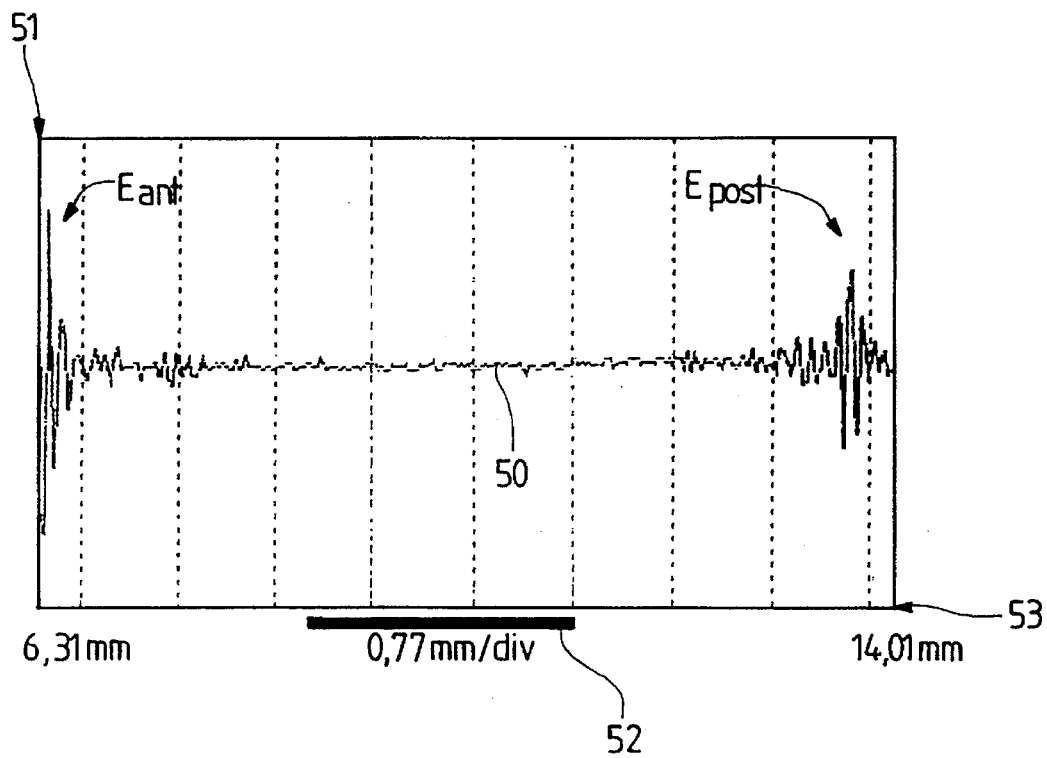
FIG. 4 shows a display of digital values corresponding to an echo signal received by the apparatus of FIG. 3; and, FIG. 5 shows the display of FIG. 4 after a group of digital values between elemental echos has been removed.

The display means 32 may be used to assist the user in the selection of these parameters. As seen in FIG. 4, a trace 50 of the echo signal received by the analog-digital converter 26 is presented to the user to help correctly position the ultrasonic transducer 21 with respect to the blood vessel 3. When the horizontal gain of the trace 50 is adjusted appropriately, each of the digital values within the range which can be treated by the calculating device 22 between consecutive pulses may be displayed. Based upon the trace 50, the user may adjust the delay from the transmission of the ultrasonic pulse until the analog-digital converter 26 is caused to commence digitizing the echo signal, thus defining the left-hand vertical axis 51 of the trace 50.

If the time between the detection of the elemental echos from the anterior wall and the posterior wall of the blood vessel 3 is too great, one or both of the elemental echos $E_{ant}$ and $E_{post}$ as partially seen in the trace 50 may fall outside the range of digital values which may be treated by the processing device 22 between consecutive pulses (as is the case illustrated in FIG. 4). To address this problem, the apparatus 20 is adapted to allow the user to select a group of digital values which are not treated. A bar 52 is displayed at the display means 32 along the horizontal axis 53 of the trace 50, which bar allows visualisation of the contiguous group of digital values to be "cut" from the trace 50. The length of the bar 52 can be adjusted by the user.

By appropriately choosing the length of the bar 52 and the delay until the analog-digital converter 26 commences digitization of the echo signals, a desired portion of the trace 50 can be removed. It is to be appreciated that the display of the trace 50 and the bar 52 represent merely one covenient way in which the user may select a group of digital values from the echo signals which are not to be treated. The calculating device 22 may automatically choose a group of digital values which are not to be treated, based on the separation between the elemental echos of the echo signals.

Once the portion of the trace 50 to be removed has been chosen, information identifying this chosen portion is sent from the calculating device 22 to the processor 29 of the analog-digital converter 26. After the predetermined delay following the transmission of each ultrasonic pulse, the digitizer 27 commences digitizing the echo signal received from the control circuit 24. Each digital value thus created is stored by the processor 29 in a separate location within the buffer memory 28. At the digital value corresponding to the start of the portion to be removed from the trace 50, the processor 29 temporarily ceases this storage. During this temporary cessation, the digitizer may continue to digitize the echo signal, but the digital values so produced are not stored. At the digital value corresponding to the end of the portion to be removed, the processor 29 once again stores the digital values from the digitizer 27 into separate memory locations in the buffer memory 28. The temporal window during which the echos are awaited accordingly remains open during a fixed total time, but this effective closure and reopening of the window enables the positioning of the elemental echos $E_{ant}$ and $E_{post}$ within the temporal window.

Figure 5:
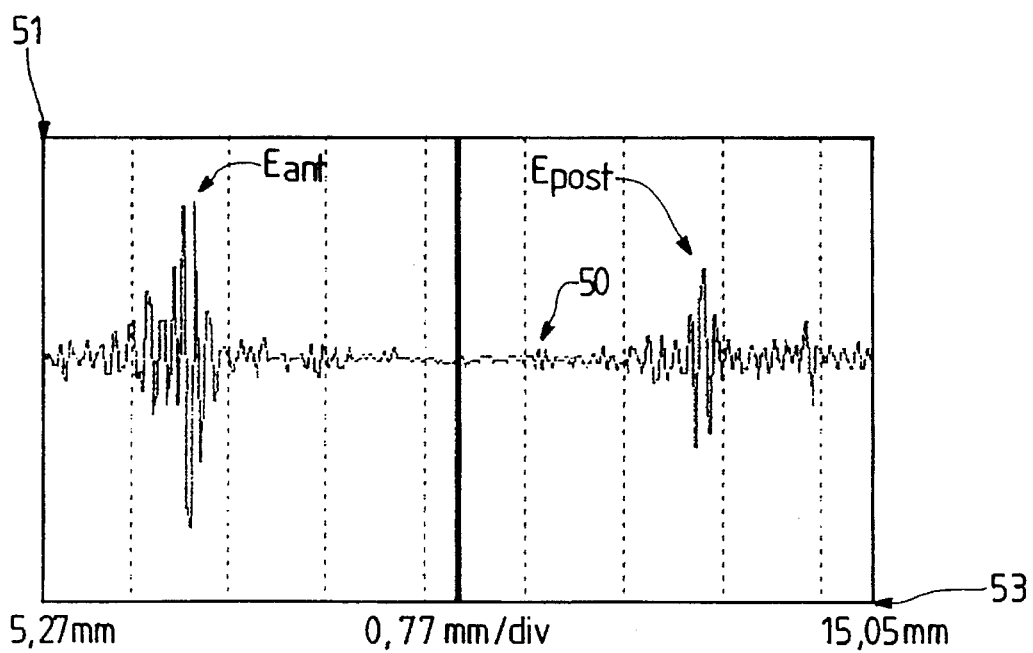

Once the maximum number of digital values from each echo signal which can be treated by the calculating device 22 have been stored, they are transferred to the calculating device 22 and stored in the memory means 31. The processing means 30 then causes the display means 32 to display the digital values stored in the memory means 31, as illustrated in FIG. 5. It can with seen that with appropriate selection of the portion to be removed from the trace 50 and the delay until the digitizing commences, the digital values corresponding to both of the elemental echos $E_{ant}$ and $E_{post}$ may be included in those digital values which can be treated by the calculating device 22. The form of the echo signals may thus be verified and monitored during operation of the apparatus 20. The echo tracker is also enabled to function correctly and automatically tracks the reference points on the echo signals during the measurement process carried out by the apparatus 20.

Alternatively, the digital values created by the digitizer 27 from the echo signals may be stored in the memory buffer 28 without a selected group of digital values between the elemental echos being firstly removed. The processing means 30 may be adapted so as to not transfer this selected group when the other digital values are transferred from the memory buffer 28 to the memory means 31. This more complicated transfer would, however, limit the time available to the processing means 30 between consecutive pulses during which the digital values may be treated.

A further alternative is to simply store the digital values received from the digitizer 27 in the memory buffer 28, and transfer these digital values from there to the memory means 31, without removing a group of digital values between the elemental echos. The processing means 30 may in this case be adapted to effectively ignore a selected group of digital values which were not to be treated. However, the time available for treatment between consecutive pulses is again reduced, due to the increased number of digital values which need to be transferred, and the more complicated—and hence slower—way in which the digital values thus stored in the memory means 31 must be handled.

The user can then proceed to measure the position of the interfaces of the blood vessel by using the apparatus 20 to carry out the measuring process described in Swiss patent application no. 2871/91. This measurement process will not be described here in detail, but can be divided into three stages, namely an initialisation stage, an assimilation stage and a processing stage. In the initialisation stage, the digital values transferred to and stored in the memory means 31 are treated so as to select a reference point in each elemental echo of the echo signal, determine for each elemental echo the temporal position of each interface producing that elemental echo, and calculate for each elemental echo the temporal interval between the position of the reference point of that elemental echo and the temporal position of the interface obtained by the processing.

In parallel with this treatment, the assimilation phase occurs in which the digital values resulting from the detection of echo signals from subsequent ultrasonic pulses are treated so as to track the temporal position of the reference points from each echo signal.

There follows then the acquisition phase in which the temporal position of each interface corresponding to each elemental echo of echo signals resulting from ultrasonic pulses subsequent to the assimilation phase are followed and memorized. Finally, an exploitation stage occurs during which the data memorized in the acquisition phase is used to provide information to the user, such as displaying the diameter of the blood vessel as a function of time.

Finally, it is to be understood that various modifications and/or additions may be made to the ultrasonic measuring apparatus without departing from the ambit of the present invention as defined in the claims appended hereto.

I claim:

1. Ultrasonic measuring apparatus comprising:

an ultrasonic transducer for emitting ultrasonic pulses at a predetermined repetition frequency towards an object having a plurality of walls, receiving echoes reflected from said walls, and producing echo signals having an plurality of elementary echo components ($E_{ant}$, $E_{post}$), digitizing means for digitizing each one of said echo signals into a series of digital values, a buffer memory coupled to said digitizing means for receiving and storing said digital values directly from said digitizing means, control means for transferring said digital values from said digitizing means into said buffer memory, memory means for receiving and storing said digital values from said buffer memory, and processing means for transferring said series of digital values stored in said buffer memory into said memory means, said processing means processing the digital values stored in said memory means between consecutive ones of said pulses, wherein said processing means further includes means for deleting a contiguous group of said digital values digitized between consecutive elementary echo components produced by said consecutive pulses from the digital values to be processed by said processing means between said consecutive pulses, said deleting means deleting said contiguous group of said digital values before the remaining digital values are processed by said processing means.

2. Ultrasonic measuring apparatus according to claim 1, wherein said deleting means deletes said group of digital values from said series of digital values prior to the storage of said digital values in said memory means.

3. Ultrasonic measuring apparatus according to claim 2, wherein said deleting means deletes said group of digital values from said series of digital values prior to the storage of said digital values in said buffer memory.

4. Ultrasonic measuring apparatus according to claim 1, further including:

user input means for selecting said group of digital values.

5. Ultrasonic measuring apparatus according to claim 1, further including:

display means for displaying said series of digital values to enable visualization of said echo signal, said display means additionally indicating said selected group of digital values prior to their removal from said digital values treated between consecutive pulses.

6. Ultrasonic measuring apparatus according to claim 2, further comprising:

user input means for selecting said group of digital values.

7. Ultrasonic measuring apparatus according to claim 3, further comprising:

user input means for selecting said group of digital values.

8. Ultrasonic measuring apparatus according to claim 2, further comprising:

display means for displaying said series of digital values to enable visualization of said echo signal, said display means additionally indicating said selected group of digital values prior to their removal from said digital values treated between said consecutive pulses.

9. Ultrasonic measuring apparatus according to claim 3, further comprising:

display means for displaying said series of digital values to enable visualization of said echo signal, said display means additionally indicating said selected group of digital values prior to their removal from said digital values treated between said consecutive pulses.

10. Ultrasonic measuring apparatus according to claim 4, further comprising:

display means for displaying said series of digital values to enable visualization of said echo signal, said display means additionally indicating said selected group of digital values prior to their removal from said digital values treated between said consecutive pulses.

* * * * *